United States Patent [19]

Krivit

[11] 4,026,308

[45] May 31, 1977

[54] DENTAL FLOSS HOLDER

[76] Inventor: Lawrence R. Krivit, 14 Orchard Drive, Armonk, N.Y. 10504

[22] Filed: Oct. 17, 1975

[21] Appl. No.: 623,443

[52] U.S. Cl. .................................................. 132/91
[51] Int. Cl.² ......................................... A61C 15/00
[58] Field of Search ............... 132/92 A, 93, 91 A, 132/92 R; 32/60

[56] References Cited

UNITED STATES PATENTS

| | | | |
|---|---|---|---|
| 1,986,371 | 1/1935 | Sharp | 132/92 R |
| 3,393,687 | 7/1968 | Whitman | 132/91 |
| 3,835,872 | 9/1974 | Daniel | 132/92 R |
| 3,908,678 | 9/1975 | Spector | 132/92 R |

*Primary Examiner*—Robert Peshock

[57] ABSTRACT

A dental floss holder comprises a substantially rectangular body having a U-shaped cut out with a pair of spaced protruding legs at one end between which the dental floss is strung. In one embodiment, the body portion includes a first pair of opposed slots at an intermediate location and a second pair of opposed slots near the base of the U-shaped cut out with said slots being located in the edges of the body to permit stringing the dental floss in a continuous manner. The end portion of the body with the protruding legs is positioned at an angle to the main portion of the body in order to facilitate use of the holder. In another embodiment of the invention, protruding elements are located between the adjacent slots on one side of the body while in a further embodiment a peculiar knuckle-type protrusion is located on each side of the holder eliminating the need for slots.

The holder is relatively inexpensive and does not require separate gripping elements to hold the dental floss in place thereby saving time and effort.

6 Claims, 7 Drawing Figures

DENTAL FLOSS HOLDER

BACKGROUND OF THE INVENTION

The invention relates to dental floss and particularly to a dental floss holder of a new and improved design.

The prior art includes U.S. Pat. Nos. 2,384,712 and 2,463,660 to J. Turenchalk which disclose a dental floss holder having an end portion comprising a pair of spaced legs, the legs being positioned at an angle to the main portion of the holder. The Turenchalk patents are directed to novel means for holding the dental floss in a taut position between the legs. Since the present invention does not involve the use of clamps it is obviously different and certainly less expensive than the prior art designs of Turenchalk.

Stewart U.S. Pat. No. 2,828,734 discloses a dental floss holder having an end portion which is mounted at an angle to the main body portion. The design also includes cut out portions between which the dental floss is strung and, furthermore, the ends of the dental floss may be wrapped around protruding horns or tied together as illustrated in the drawings. The present invention does not require the use of such horns in the precise environment of the reference. In this invention the dental floss is held taut by the wrapping procedure disclosed herein and a different structural arrangement.

Also of interest is U.S. Pat. No. 3,387,615 to MacKew which illustrates a dental floss holder having its end portion angled at a position to the main body portion and cut out portions between which the dental floss is strung and then secured in a product horn 38. This patent does not disclose an end cut out nor does it disclose the same wrapping technique as disclosed in the present invention.

SUMMARY OF THE INVENTION

The present invention pertains to an improved dental floss holder which is relatively inexpensive and simple to use. The invention comprises a substantially rectangular main body portion of a material such as plastic which includes a pair of spaced protruding legs at one end between which the dental floss is strung. The body portion includes a first pair of slots located at an intermediate portion of the body and a second pair of slots located near the base of the protruding legs. The slots are located in the edges of the body to permit anchoring of the dental floss therein as it is strung in a continuous manner starting in one of the intermediate slots. The end portion of the body including the protruding legs is located at an angle to the body and includes grooves at the external edges thereof to accomodate the dental floss. The dental floss is strung between the legs and is held in a taut position by the slots. The angular arrangement of the end portion is designed to facilitate the use of the holder, particularly in hard to get at locations.

In another embodiment of the invention, protruding elements are located between the adjacent slots on one side of the body while in a further embodiment, a peculiar knuckle-type protrusion is located on each side of the body eliminating the need for slots.

Accordingly, an object of this invention is to provide a new and improved dental floss holder.

Another object of this invention is to provide a relatively inexpensive dental floss holder having a particularly advantageous configuration to facilitate the use of dental floss.

A more specific object of this invention is to provide a new and improved dental floss holder wherein the dental floss may be strung in one continuous rapid motion to provide a taut stretch of dental floss between the spaced legs of the holder without the use of separate clamping means.

BRIEF DESCRIPTION OF THE DRAWINGS

Other objects and advantages may be seen from the following description when viewed in conjunction with the accompanying drawings wherein.

DETAILED DESCRIPTION OF THE INVENTION

Figure 1:
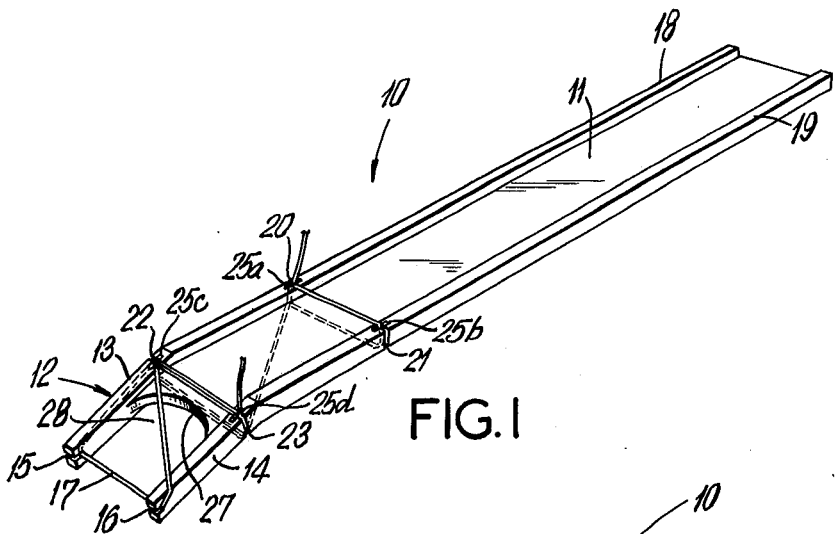
FIG. 1 is a perspective view of the dental floss holder comprising the present invention.
Figure 2:
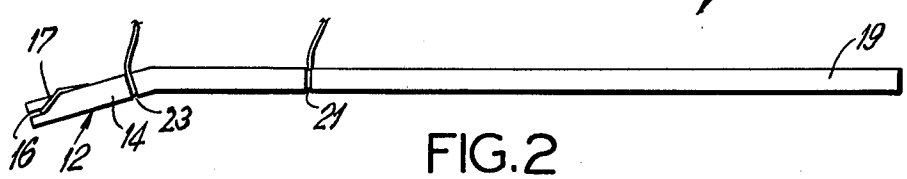
FIG. 2 is a side view of the invention.
Figure 3:
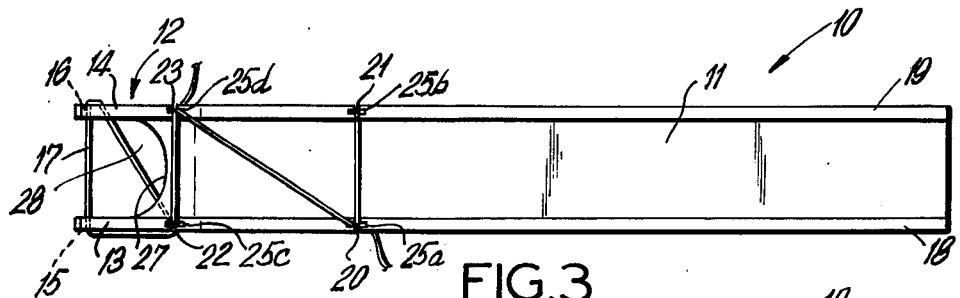
FIG. 3 is a bottom view illustrating the wrapping of the dental floss on the holder.

Referring to FIGS. 1 - 3 of the drawings, the invention comprises a dental floss holder 10 having a main body portion 11 of substantially rectangular configuration with one end 12 of the body 11 positioned at a predetermined angle thereto in order to reach hard to get at locations. The end portion 12 includes a U-shaped cut out 28 forming a pair of oppositely positioned legs 13 and 14 having transverse slots 15 and 16 located in the ends thereof and between which a strand of dental floss 17 is strung.

The body 11 includes enlarged rectangular rib portions 18 and 19 along each side thereof which serve to strengthen the body 11 which is of relatively thin material such as plastic. Transverse slots 20 and 21 are located opposite one another in the ribs 18 and 19 at an intermediate portion of the body 11 and additional slots 22 and 23 are located opposite one another in the ribs 18 and 19 near the base 27 of the U-shaped cut out 28. The slots 20, 21, 22 and 23 each include a perpendicular portion 25a, 25b, 25e and 25d in the ribs 18 and 19 which serve to secure the dental floss 17 in the various slots.

In operation, a length of dental floss 17 is initially strung between oppositely positioned slots 20 and 21 and is then brought up and about the body 11 into slot 23, across the slot 22 and up along the leg 13 of the U-shaped portion 28. The dental floss 17 is then strung between the legs 13 and 14 while being anchored in slots 15 and 16. The floss 17 is then wrapped several times around paired slots 22–23 and/or slots 20–21. The dental floss 17 is thus held taut between the legs 13 and 14 particularly by the slots 20, 21, 22 and 23 and their perpendicular portions 25a–d. This simple wrapping procedure secures the dental floss 17 in place without the use of auxiliary elements such as clamps and permits the use of a simple molded plastic holder 10 which is lightweight and inexpensive. The configuration of the holder 10 also facilitates the ready use of the holder 10 in applying dental floss 17 to hard to get at locations.

Figure 4:
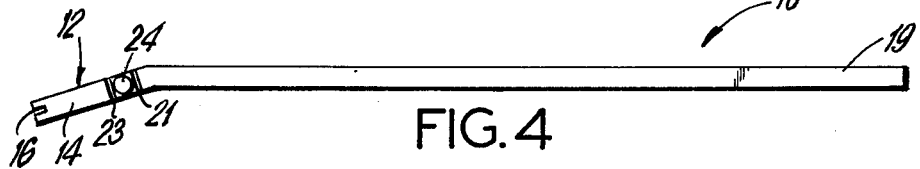
FIG. 4 is a side view of another embodiment of the invention.
Figure 5:
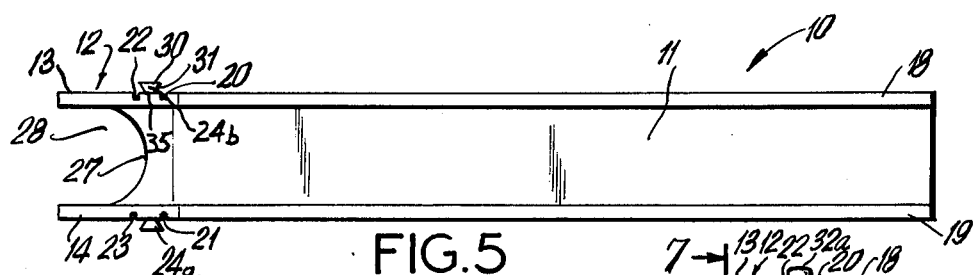
FIG. 5 is a plan view of the embodiment of FIG. 4.

A second embodiment of the invention is shown in FIGS. 4 and 5 wherein a pair of oppositely located protrusions or knobs 24a and 24b are located on the end 12 between pairs of transverse slots 20–21 and 22–23. The knobs 24a, 24b are substantially frustoconical in configuration with the outer base 30 being larger than the portion 35 joining with the ribs 18 and 19. The sloping walls 31 serve to anchor the dental floss 17 adjacent the ribs 18 and 19. In this embodiment less wrapping is required since the protrusions 24 assist in securing the dental floss 17 in place between the legs 13 and 14 of the U-shaped portion 28. The dental floss 17 would be strung between paired slots 20, 21, then slots 22, 23, and finally about one of the knobs 24a or 24b before being brought up and strung between the legs 13 and 14. Finally, the dental floss 17 would be wrapped around one of the knobs 24a or 24b and then between paired slots 20, 21 and/or 22, 23 to provide a final anchor. Other wrapping sequences could, of course, be employed and this flexibility is one of the advantages of this invention. The perpendicular slot portions 25a, 25b, 25c and 25d of the first embodiment are not needed in this alternate embodiment.

Figure 7:
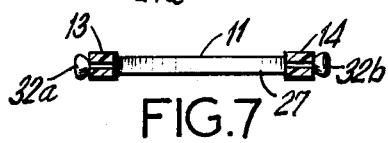
Figure 6:
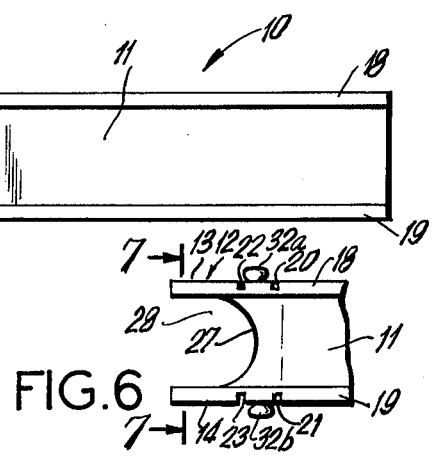
FIG. 6 is a partial plan view of a further embodiment of the invention, and, FIG. 7 is a view taken along lines 6—6 of FIG. 6.

A still further embodiment is shown in FIGS. 6 and 7 wherein a pair of shaped protrusions or knuckles 32a and 32b are located on the rib portions 18 and 19 of the body 11 on the end 12 of the holder 10. The knuckles 32a and 32b are so structured that the dental floss in anchored securely at the base of said almost eliptical knuckles by friction prior to being strung between the legs 13 and 14 of the U28 and thus, the use of slots may be eliminated altogether. The embodiment, as shown, in FIGS. 6 and 7 does include slots 20, 21, 22 and 23 as an option. The knuckles 32a and 32b are of generally curved configuration with the floss being anchored between the lower portion of the knuckles 32a and 32b and the ribs 18 and 19. Less dental floss 17 is also required with this embodiment but more importantly, the wrapping is simpler and faster.

While the invention has been explained by a detailed description of certain specific embodiments, it is understood that various modifications and substitutions can be made in any of them within the scope of the appended claims which are intended also to include equivalents of such embodiments.

What is claimed is:

1. A dental floss holder comprising:
   an elongated substantially rectangular body having an end portion at a predetermined angle to the main body portion, said end portion having a U-shaped cut out forming a pair of juxtaposed legs and including a pair of transverse slots in each leg thereof, and wherein,
   the main body portion includes a rib extending along each side of the main body portion, said ribs having a pair of oppositely arranged slots at an intermediate portion of the main body, and,
   a second pair of oppositely arranged slots in the ribs on the end portion of the body, and,
   whereby dental floss may be securely wrapped about the holder and held in a taut condition between the legs, said dental floss being initially wrapped within the slots in the intermediate portion of the main body, then within the slots in the end portion and then finally being inserted in the slots in the legs and finally wrapped within the oppositely arranged slots.

2. A dental floss holder in accordance with claim 1 wherein:
   the slots in the ribs each include a transverse portion extending into the ribs and a perpendicular slot portion in said ribs essentially forming a T-shaped slot to securely lock the dental floss in the perpendicular portion.

3. A dental floss holder in accordance with claim 2 wherein:
   the main body portion comprises a relatively thin rectangular element and the ribs each comprise a narrow enlarged rectangular element joined to the outer edge of the body portion.

4. A dental floss holder comprising:
   a main body portion of a substantially rectangular configuration having an end portion at a predetermined angle thereto and a rib extending along each side thereof, and,
   wherein the end portion includes a pair of juxtaposed legs having a U-shaped cut out section therebetween and transverse slots at the ends of the legs between which dental floss may be strung in a taut condition and,
   wherein the ribs at the end portion include first and second pairs of juxtaposed slots and a protrusion extending outwardly from each rib therebetween to aid in anchoring the dental floss.

5. A dental floss holder in accordance with claim 5 wherein:
   the protrusions are of a substantially inverted frustoconical configuration with the larger base section forming the outer surface of the protrusion to guide the dental floss towards the base section thereof.

6. A dental floss holder comprising:
   a main body portion of a substantially rectangular configuration having an end portion at a predetermined angle thereto and a rib extending along each side thereof, and,
   wherein the end portion includes a pair of juxtaposed legs having a U-shaped cut out section therebetween and transverse slots at the ends of the legs between which dental floss may be strung in a taut condition and,
   wherein the ribs at the end portion each include a substantially eliptical knuckle extending outwardly and having a lower portion joining the ribs with a narrow spacing therebetween to hold the dental floss securely as it is strung therebetween and up through the transverse slots in the legs.

* * * * *